(12) United States Patent
Mueller-Hartmann et al.

(10) Patent No.: US 8,895,152 B2
(45) Date of Patent: Nov. 25, 2014

(54) METHOD FOR GENERATING AN ELECRICALLY CONTACTABLE AREA ON A DOPED POLYMER AND FORMED BODY PRODUCED BY THIS METHOD

(75) Inventors: Herbert Mueller-Hartmann, Cologne (DE); Ewald Fernbach, Pulheim (DE); Gregor Siebenkotten, Frechen-Koenigsdorf (DE)

(73) Assignee: Lonza Cologne GmbH, Cologne (DE)

( * ) Notice: Subject to any disclaimer, the term of this patent is extended or adjusted under 35 U.S.C. 154(b) by 890 days.

(21) Appl. No.: 10/972,294

(22) Filed: Oct. 25, 2004

(65) Prior Publication Data
US 2005/0214562 A1   Sep. 29, 2005

(30) Foreign Application Priority Data
Oct. 24, 2003  (EP) .................................... 03024343

(51) Int. Cl.
| | |
|---|---|
| B32B 15/08 | (2006.01) |
| C12M 1/42 | (2006.01) |
| H01C 1/142 | (2006.01) |
| A61N 1/30 | (2006.01) |
| A61N 1/32 | (2006.01) |
| A61N 1/04 | (2006.01) |

(52) U.S. Cl.
CPC .............. C12M 35/02 (2013.01); *A61N 1/0496* (2013.01); *A61N 1/0472* (2013.01); *A61N 1/0408* (2013.01); *H01C 1/142* (2013.01); *A61N 1/30* (2013.01); *A61N 1/327* (2013.01)
USPC ............ 428/626; 428/615; 422/554; 356/246

(58) Field of Classification Search
USPC ......... 264/109, 119, 299, 319, 320, 322, 327, 264/328.1
See application file for complete search history.

(56) References Cited

U.S. PATENT DOCUMENTS

| | | | |
|---|---|---|---|
| 3,917,149 A | * | 11/1975 | Breton et al. .............. 228/124.1 |
| 4,570,055 A | | 2/1986 | McMills |

(Continued)

FOREIGN PATENT DOCUMENTS

| | | |
|---|---|---|
| DE | 199 42 347 A1 | 3/2001 |
| DE | 100 33 507 A1 | 1/2002 |

(Continued)

OTHER PUBLICATIONS

Loomis-Husselbee JW, Cullen PJ, Irvine RF, Dawson AP, *Electroporation can cause artefacts due to solubilization of cations from the electrode plates. Aluminum ions enhance conversion of inositol 1,3,4,5-tetrakisphosphate into inositol 1,4,5-trisphosphate in electroporated L1210 cells.* Biochem. J. (1991) 277:883-885.

(Continued)

*Primary Examiner* — Jeffrey Wollschlager
(74) *Attorney, Agent, or Firm* — Joyce von Natzmer; Agris & von Natzmer LLP

(57) ABSTRACT

The invention relates to a method for generating at least one electrically contactable area on a polymer which is doped with a conductive substance, wherein a contact material is applied onto the polymer, which has a lower specific resistance at 23° C. than the polymer. According to the invention the contact material is applied onto the polymer so tightly that close contact between the contact material and the conductive substance is achieved. Due to the tight application of the contact material, which has a lower specific resistance than the polymer, the input resistance of the doped polymer is effectively reduced. The invention further concerns a formed body made of a polymer which is doped with a conductive substance, which has at least one contactable area, within which a contact material is applied onto the polymer, which has a lower specific resistance at 23° C. than the polymer. According to the invention the contact material is applied onto the polymer so tightly that it is in close contact to the conductive substance. Such formed body has a significantly reduced input resistance.

12 Claims, 7 Drawing Sheets

(56) References Cited

U.S. PATENT DOCUMENTS

| | | | |
|---|---|---|---|
| 4,605,536 A * | 8/1986 | Kuhnert et al. | 422/549 |
| 4,761,541 A * | 8/1988 | Batliwalla et al. | 219/528 |
| 4,765,874 A * | 8/1988 | Modes et al. | 205/635 |
| 4,859,263 A * | 8/1989 | Dziurla et al. | 156/233 |
| 5,128,257 A * | 7/1992 | Baer | 435/173.6 |
| 5,410,204 A * | 4/1995 | Imabayashi et al. | 310/323.13 |
| 5,849,129 A * | 12/1998 | Hogge et al. | 156/244.27 |
| 5,890,679 A | 4/1999 | Chethik | |
| 6,217,732 B1 * | 4/2001 | Schuh et al. | 204/490 |
| 6,503,432 B1 * | 1/2003 | Barton et al. | 264/173.16 |
| 6,713,154 B1 * | 3/2004 | Tsunogae et al. | 428/131 |
| 6,830,848 B1 * | 12/2004 | Fujiwara et al. | 429/213 |
| 2002/0025573 A1 * | 2/2002 | Maher et al. | 435/287.1 |
| 2002/0130673 A1 | 9/2002 | Pelrine et al. | |
| 2002/0164776 A1 | 11/2002 | Beichmann et al. | |
| 2002/0197917 A1 * | 12/2002 | Mukai et al. | 439/884 |
| 2004/0048152 A1 * | 3/2004 | Yata et al. | 429/162 |
| 2004/0081889 A1 * | 4/2004 | Lee et al. | 429/233 |
| 2005/0064578 A1 | 3/2005 | Muller-Hartmann et al. | |

FOREIGN PATENT DOCUMENTS

| | | | |
|---|---|---|---|
| DE | 101 16 211 A1 | 10/2002 | |
| DE | 102 08 188 A1 | 9/2003 | |
| DE | 10208188 * | 9/2003 | C12M 1/00 |
| EP | 0 307 007 B1 | 3/1989 | |
| EP | 0 402 554 B1 | 12/1990 | |
| EP | 0778046 A2 | 6/1997 | |
| EP | 1 100 295 A | 5/2001 | |
| WO | WO 00/57680 A | 9/2000 | |

OTHER PUBLICATIONS

Stapulionis R., *Electric pulse-induced precipitation of biological macromolecules in electroporation*. Bioelectrochem Bioenerg. (Feb. 1999) 48(1):249-54.

* cited by examiner

METHOD FOR GENERATING AN ELECRICALLY CONTACTABLE AREA ON A DOPED POLYMER AND FORMED BODY PRODUCED BY THIS METHOD

FIELD OF THE INVENTION

The invention relates to a method for generating at least one electrically contactable area on a polymer which is doped with a conductive substance, wherein a contact material is applied onto the polymer, said contact material having a lower specific resistance at 23° C. than the polymer. The invention further concerns a formed body made of a polymer which is doped with a conductive substance, which has at least one contactable area, within which a contact material is applied onto the polymer, wherein said contact material has a lower specific resistance at 23° C. than the polymer.

BACKGROUND OF THE INVENTION

Electroconductive polymers are known and enjoy increasing popularity, in particular also as material for producing electrodes for generating electric fields in various applications.

For example, an assembly for electrical arrangements is known from EP 0 307 007 B1, which comprises conductive components having different specific resistances. A resistor made of a conductive polymer, i.e. a mixture of an organic polymer and a conductive filler, which has a relatively high specific resistance at 23° C. of 1-500.000 ohm×cm, is here provided with a contact layer consisting of a conductive material which has a specific resistance that is lower than the specific resistance of the resistor, i.e. a specific resistance between $2.5 \times 10^{-5}$ and $1 \times 10^{-3}$ ohm×cm. The contact layer also consists of a conductive polymer which is doped with a metal, e.g. silver, or a carbon-based material, e.g. graphite. The contact layer is disposed onto the resistor in the form of band-like electrodes which interlock like fingers. Conductor rails are provided as contacting elements, which consist of a stretched net made of metal and which are folded around the contact layer and the electrodes formed therefrom, respectively. The area at the edges of the electrodes acts as contact area. Although, with this solution, the input resistance of the resistance layer is reduced by application of a contact layer having lower specific resistance, this contact layer itself consists of a doped polymer and hence has still a relatively high input resistance as well. This is particularly true if demixing close to the surface occurs when the contact layer is injection-moulded. Furthermore, the contact layer is here contacted via close-fitting conductor rails, i.e. stretched metal nets, and is thus not comparable to a dot-like contact. But there are many applications wherein dot-like contacting, e.g. via spring contacts, is necessary due to specific requirements or constructive conditions. But in this case, dot-like contacting of the disclosed contact layer would result in a burn-in of the contacting elements to the contact points when very high voltages would be applied.

Since metal ions are emitted from electrodes made of metal during electric discharge, particularly in the field of biological applications, electrodes made of conductive synthetic material are advantageous compared to commonly used metal electrodes. With the treatment of living cells, for example with electroporation or electrofusion, metal ions emitted into the respective cell suspension can either cause undesirable stimulation of the cells at lower concentrations or, at higher concentrations, act toxic on the cells. For instance, when cuvettes made of aluminium are used a negative effect due to the release of $Al^{3+}$ ions could be demonstrated (Loomis-Hasselbee et al., Biochem J 1991, 277 (Pt 3), 883-885). Furthermore, if using cuvettes having electrodes made of metal generation of metal hydroxides or complexes of metal ions with biological macromolecules may occur (Stapulionis, Bioelectrochem Bioenerg 1999, 48(1), 249-254), what is often undesirable as well.

DE 102 08 188 A1 discloses containers with electrodes made of doped polymers. The doped polymers are polymers which are blended with conductive substances such as carbon fibers, graphite, carbon black (soot) or carbon nanotubes. Although those doped polymers have lower conductivity compared to intrinsically conductive polymers, it is a benefit that they are mouldable, i.e. that processing by the use of injection-moulding is possible. Thus, such doped polymers are variously useful and allow a cost-effective production of electrodes by injection-moulding. But it is a problem with such electrodes that demixing occurs during the injection-moulding process so that the concentration of the conductive dope is relatively low at the surface of the electrodes. Therefore, respective electrodes have a very high input resistance so that very high voltages have to be applied in order to achieve a sufficient current flow. But when usual dot-like contacting of these electrodes is used, for example via spring contacts, the contacts burn-in to the surface of the electrodes due to the high voltages applied so that the electrodes become unusable.

DE 101 16 211 A1 discloses a device for fusing living cells within an electric field, wherein the electrodes are also made of a doped synthetic material, i.e. a plastic material which is blended with carbon. The electrodes are connected to a voltage source via dot-like contact points and corresponding lead wires. Thus, also in this case it is a disadvantage that burn-in to the surface of plastic electrodes would occur if voltages should be applied, which are higher than those necessary for electrofusion. For example, to reach field strengths which are sufficient for certain applications in electroporation significantly higher voltages have to be applied to the electrodes. Field strengths of 2-10 kV/cm may be necessary, for instance, for the transfer of biologically active molecules into the nucleus of living cells. The voltage necessary to reach such field strengths would also in this case result in a burn-in of the contact points if the known polymer electrodes are contacted dot-like.

It is thus an object of the invention to overcome the existing deficiencies and to provide a method as identified above, which allows an effective reduction of the input resistance of the polymer within the contactable area in a simple and cost-effective manner. It is a further object of the invention to provide a formed body of the initially mentioned kind, which has a low input resistance, and which can be produced easily and cost-effectively.

SUMMARY OF THE INVENTION

According to the invention this object is solved by a method as mentioned above, wherein the contact material is applied onto the polymer so tightly that close contact between the contact material and the conductive substance is achieved. Due to the tight application of the contact material, which has a lower specific resistance than the polymer, the input resistance of the doped polymer is effectively reduced, whereas the close contact between the contact material and the polymer actually results in a merger of both components. Thus, an intensive contact with the conductive dope of the polymer is achieved. The dope of the polymer, which, for example, may consist of carbon fibres and/or graphite, has a specific concentration within the polymer, e.g. 75% w/w, which ensures that the doped polymer provides a sufficient conductibility. Since demixing occurs at the surface of the polymer, i.e. the concentration of the dope at the surface of the material is significantly lower than beneath, e.g. if the doped polymer is injection-moulded, the contact material has to be applied to the polymer so tightly that contact is established between the contact material and at least approximately the specific concentration of the conductive dope. In this manner, the demixed zone at the surface consisting merely a modicum of conductive material is bypassed so as to effectively reduce the input resistance. In order to effectively reduce the input resistance, in particular for applications which require very high field strengths of 2-10 kV/cm between both electrodes, the contact material has to be applied to the polymer so tightly that a connection to the dope of the polymer is established by the contact material, which is sufficient to keep the temperature at the contact area between the polymer and the contact material below the softening point of the doped polymer while conducting electric current. Due to this measure it is possible to effectively contact a polymer, which is doped with a conductive substance, dot-like within the contactable area, i.e. for example via a wire or a spring contact, without burn-in of the contacts to the surface of the polymer, even if high voltages are applied.

In an advantageous embodiment of the invention the contact material is applied while being exposed to a temperature which is enhanced compared to room temperature, preferably a temperature which is higher than the softening temperature of the doped polymer, so as to establish a very close contact between the contact material and the doped polymer. In the ideal case, both materials may merge with each other. Additionally, impression or intrusion of the contact material into the surface of the polymer is allowed hereby so that the contact with the dope of the polymer, i.e. the conductive material, can be intensified so as to further reduce the input resistance.

If the contact material is applied under pressure the contact between the contact material and the doped polymer can get much closer what results in a further advantageous reduction of the input resistance. In this case, the contact material may be preferably pressed onto the polymer.

In a particularly advantageous embodiment of the invention it is further provided that the surface of the polymer is at least partially enlarged by mechanical and/or chemical treatment before the contact material is applied. Thereby, the surface of the polymer can be roughened by mechanical invasion. This measure facilitates the application of the contact material and additionally ensures an intensified interlocking of both components.

The contact material should preferably have a very low specific resistance at 23° C., for example below $1 \times 10^{-5}$ Ohm·cm. The specific resistance should be preferably in the range from $1 \times 10^{-6}$ to $2 \times 10^{-6}$ Ohm·cm.

In a further advantageous embodiment of the invention it is provided that the contact material is a foil, preferably a metal foil, in particular a copper foil, or a foil made of an intrinsically conductive plastic material. By using a foil the method according to the invention may be simplified, whereas additionally a very thin and tight-fitting contact layer is generated. Copper may be a particularly advantageous contact material since it has a very low specific resistance of about $1.7 \times 10^{-6}$ Ohm·cm at 23° C. Furthermore, Copper is easily processable and inexpensive.

In a particular embodiment of the invention the polymer may be coated with a contact material which comprises an intrinsically conductive plastic material, whereby a very intensive contact between the polymer and the contact material can be established in a simple and cost-effective manner. This embodiment is further advantageous when metal cannot, or shall not, be used as contact material.

In both embodiments described above the intrinsically conductive plastic material may be, for example, polyaniline, polyacetylene, poly-para-phenylene, poly-para-phenylensulfide, polypyrroles, poly-thiophene or polypropylene, or at least based on one or several of these polymers.

Alternatively, the contact material may be a fluid or a suspension, preferably suspended metal, particularly preferred a colloidal silver suspension. But it is, for instance, also possible to apply a drop of mercury onto the polymer. This is a very simple and economic method which could be advantageous with very specific applications.

In a further alternative embodiment of the invention it is provided that the contact material is a metal plate, preferably a copper plate, which is pressed onto the polymer. Before applying the contact material a carbon-based material, preferably at least one graphite sheet, may be placed between the contact material and the polymer, which effectively reduces the input resistance of the polymer. In a special embodiment of the invention the metal plate is heated before pressing, preferably to a temperature which is higher than the softening temperature of the polymer, so as to allow impression of the metal plate into the surface of the polymer in order to intensify the contact with the dope.

In a particular embodiment of the method according to the invention the contact material may be embossed onto the polymer under heat using an embossing die, i.e. for example applied by hot-embossing. The contact material and at least a part of the polymer may be thereby heated to a temperature which is higher than the softening temperature of the polymer. The contact material is subsequently applied onto the surface of the polymer under pressure using an embossing die. Finally, the embossing die is lifted after cooling down to a temperature which is lower than the softening temperature of the polymer. While hot-embossing the contact material and/or at least one part of the polymer and/or the embossing die may be heated to a temperature between 100 and 300° C. A pressure between 50 and 100 $N/mm^2$ or between 100 and 500 $N/mm^2$ may be applied to the embossing die. Alternatively, while embossing, at first a pressure between 50 and 100 $N/mm^2$, preferably 70 and 90 $N/mm^2$, and subsequently, during the cooling period, a pressure between 100 and 500 $N/mm^2$, preferably 350 and 450 $N/mm^2$, may be applied to the embossing die. Embossing of the contact material under heat, for example hot-embossing, can take place, at least temporarily, in a vacuum or in a nitrogen atmosphere. In any case, hot-embossing is an effective and inexpensive embodiment of the method according to the invention.

In an advantageous embodiment of the invention it is provided that the contact material is applied onto the polymer by an adhesion-mediating layer which preferably has a low specific resistance so as to improve the contact between the contact material and the polymer. The adhesion-mediating layer may advantageously be a conductive material, for example an electroconductive adhesive or the like.

According to the invention the object of the invention is further solved by a formed body as mentioned above, wherein the contact material is applied onto the polymer so tightly that it is in close contact with the conductive substance. Such formed body has a significantly reduced input resistance and thus, can be effectively contacted dot-like, i.e. via a wire or a spring contact, without burn-in of the contacts to the surface of the polymer when high voltages are applied. The contact material has to be applied to the polymer so tightly that the temperature at the contact area between the contact material and the polymer is kept below the softening point of the doped polymer while conducting electric current. With the formed body according to the invention this result is ensured by the fact that the contact material has established a very close, i.e. intensive, connection to the dope of the polymer, which effectively reduces the input resistance of the polymer.

In an advantageous embodiment of the invention the contact material may be a metal, preferably copper, or an intrinsically conductive plastic material, because these materials have a low specific resistance and can be easily processed. The contact material should have a specific resistance at 23° C. below $1 \times 10^{-5}$ Ohm·cm, preferably between $1 \times 10^{-6}$ and $2 \times 10^{-6}$ Ohm·cm.

In order to further reduce the input resistance of the formed body according to the invention a carbon-based material, preferably a graphite sheet, or an adhesion-mediating layer having a low specific resistance, may be disposed between the polymer and the contact material, which each mediate an intensive contact with the conductive dope of the polymer. In an advantageous embodiment the adhesion-mediating layer may be a conductive material, for example an electroconductive adhesive or the like.

The polymer is preferably doped with carbon fibers, graphite, carbon black and/or carbon nanotubes, wherein the overall concentration of the dope in the polymer is between 50 and 80% w/w. The doped polymer should thereby have a specific resistance at 23° C. in the range from about 0.4 to 1.0 ohm×cm, preferably 0.46 ohm×cm. If such doped polymer is processed by injection-moulding the concentration of the dope at the surface is reduced by demixing. The surface resistance is thus relatively high, i.e. for example in the range from 2 to 10 ohm, in particular between 8 and 8.5 ohm. This input resistance has to be reduced by the tight application of the contact material so as to limit the total resistance of the formed body according to the invention.

The polymer may be, for instance, polycarbonate, polyetheretherketone, polypropylene, polyamide, preferably polyamide 6 or polyamide 66, polyphenylenesulfide or a mixture of these polymers, or at least based on one or several of these polymers.

The intrinsically conductive plastic material may be, for example, polyaniline, polyacetylene, poly-para-phenylene, poly-para-phenylensulfide, polypyrroles, poly-thiophene or polypropylene, or at least based on one or several of these polymers.

The formed body according to the invention preferably acts as an electrode or a similar member being necessary for conducting electric current. The formed body may also be part of a cuvette or at least of one reaction chamber of a multiwell plate, preferably in the form of an electrode, e.g. for electroporation or electrofusion of living cells, in particular for high throughput applications.

Table 1 shows characteristics of formed bodies according to the invention, which are produced by the method according to the invention, compared to respective formed bodies without applied contact material. Electrodes made of doped polymer are compared when contacted via spring contacts made of brass. At first, electrodes without any contact material or intermediate layer were tested. Using a voltage of 1000 V the spring contacts obviously burned-in to the contact area of the electrodes. In a further experiment, the electrodes were placed into an arrangement wherein contacting was not established directly via the spring contacts but via a copper foil which was applied to the contact area of the electrodes under low pressure. Also in this approach a burn-in of the copper foil to the contact area of the doped polymer could be observed, even though at a lower level. In the various embodiments of the formed bodies according to the invention, i.e. the electrodes produced by the method according to the invention, no burn-in of the spring contacts or the contact material to the contact area of the doped polymer could be observed under same conditions. Thus, by tightly applying the respective contact material onto the doped polymer a burn-in of a contact element used can be certainly avoided, even if a high voltage of 1000 V is applied.

TABLE 1

Avoiding of burn-in at the surface of formed bodies acting as electrodes, which are made of doped polymer (Polyamide 6 with carbon fibers and graphite)

| Kind of Contact | Direct Voltage applied; Flown Charge | Burn-in; Damages on surface |
|---|---|---|
| Spring Contact (Brass) | 1000 V; 5 mC | Yes; significant |
| Copper Foil Adaptor (about 20 mN/mm$^2$) | 1000 V; 5 mC | Yes; minor |
| Copper Plates (about 2 N/mm$^2$)* | 1000 V; 5 mC | No |
| Copper Plates + Graphite (about 2 N/mm$^2$)** | 1000 V; 5 mC | No |
| 55 μm Copper Foil, hot embossed, 100 mm$^2$ | 1000 V; 5 mC | No |
| 55 μm Copper Foil, hot embossed, 8 mm$^2$ | 1000 V; 5 mC | No |

*Contact Area about 100 mm$^2$
**Graphite: Density 1 g/cm$^3$, 1 mm Thickness, 100 mm$^2$ Contact Area on polymer

BRIEF DESCRIPTION OF THE DRAWINGS

The invention is described below in detail with reference to the drawings.

In the figures

Figure 4:
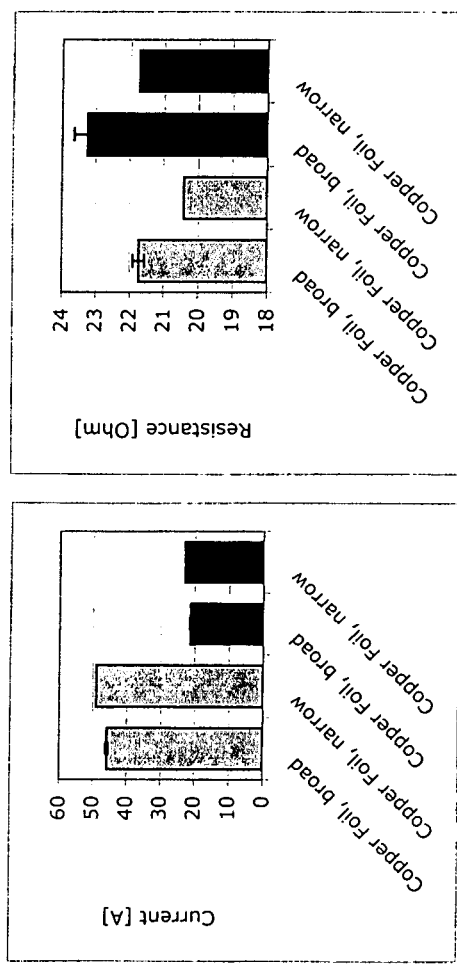
Figure 5:
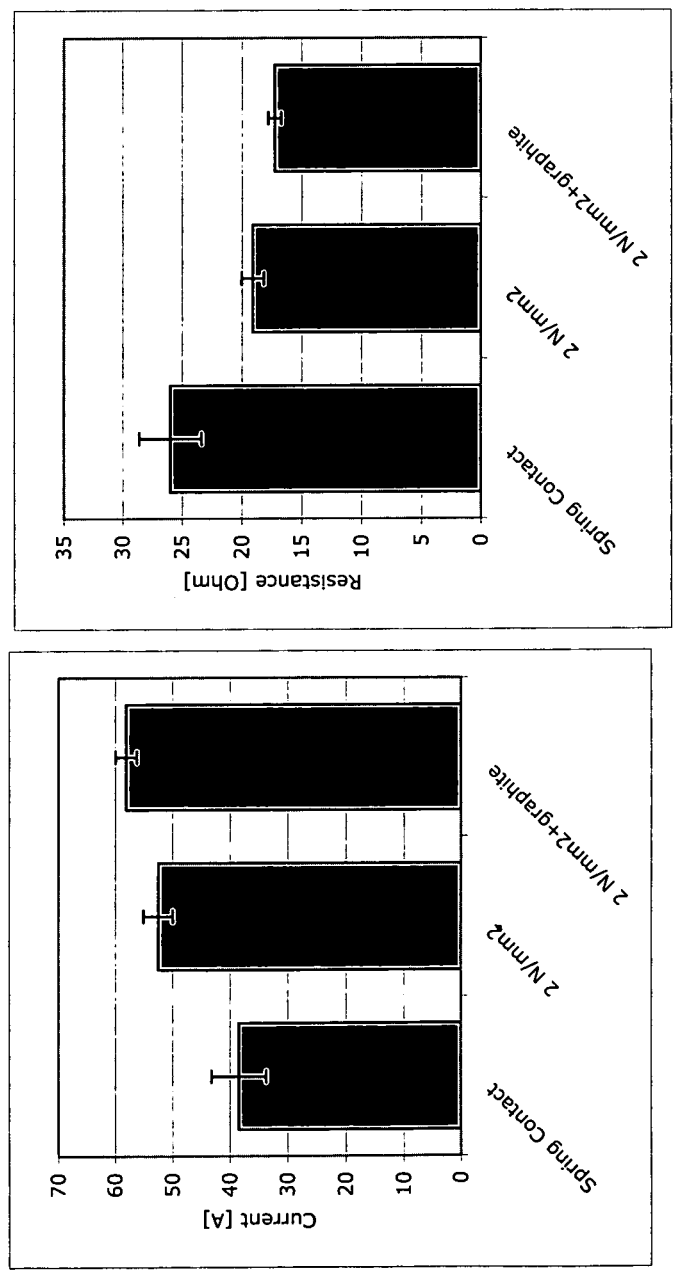
Figure 6:
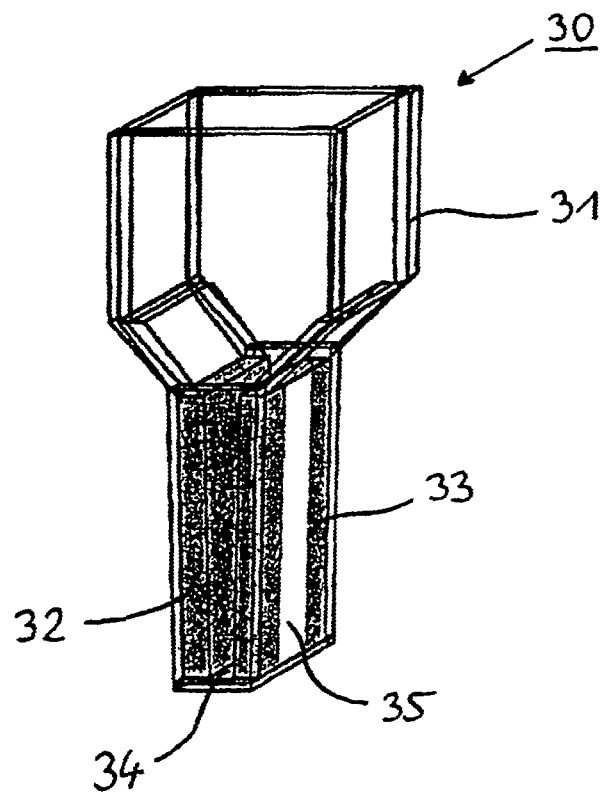
Figure 7:
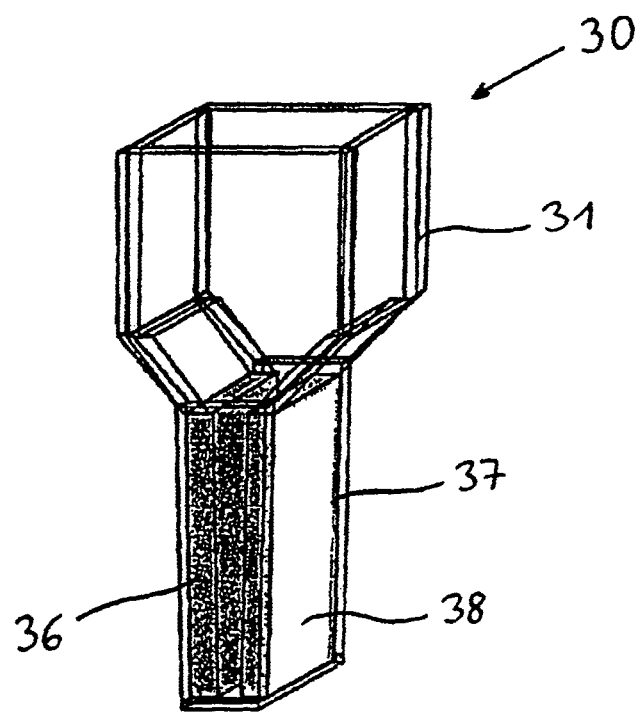

B: electrolyte solution having a specific conductivity of 17.02 mS/cm, n=2,

FIG. 4 shows bar diagrams of current strength and resistance of a comparison of the conductivity of polymer cuvettes comprising copper foils which are applied to different contact areas of the doped polymer by the method according to the invention; broad=100 mm$^2$ and narrow=18 mm$^2$, gap length of the cuvettes=1.5 mm, volume of the electrolyte solution=100 μl, specific conductivity of the electrolyte solution=12.75 mS/cm, thickness of the copper foils=55 μm, gray bars=1000 V Direct Voltage, black bars=500 V Direct Voltage, n=2, FIG. 5 shows bar diagrams of current strength and resistance of polymer cuvettes equipped with electrodes made of doped polymer, which are produced by the method according to the invention, and which are contacted by copper plates pressed onto the electrodes with or without intermediate layer, in comparison with spring contacts; gap length of the polymer cuvettes=1.5 mm, volume of the electrolyte solution=100 µl, specific conductivity of the electrolyte solution=17.02 mS/cm, applied voltage=1000 V Direct Voltage, n=3, a) spring contact made of brass,
b) solid copper plates which are pressed onto the electrodes with an estimated pressure of 2 N/mm$^2$,
c) copper plates pressed onto the electrodes with an estimated pressure of 2 N/mm$^2$, wherein graphite sheets having a density of 1 g/cm$^3$, a thickness of 1 mm, and a surface area of about 100 mm$^2$, are placed between the copper plates and the polymer electrodes, FIG. 6 shows a perspective view of a cuvette comprising formed bodies according to the invention, and FIG. 7 shows a perspective view of the cuvette according to FIG. 6 comprising a further embodiment of formed bodies according to the invention.

DESCRIPTION OF VARIOUS AND PREFERRED EMBODIMENTS OF THE INVENTION

Figure 1:
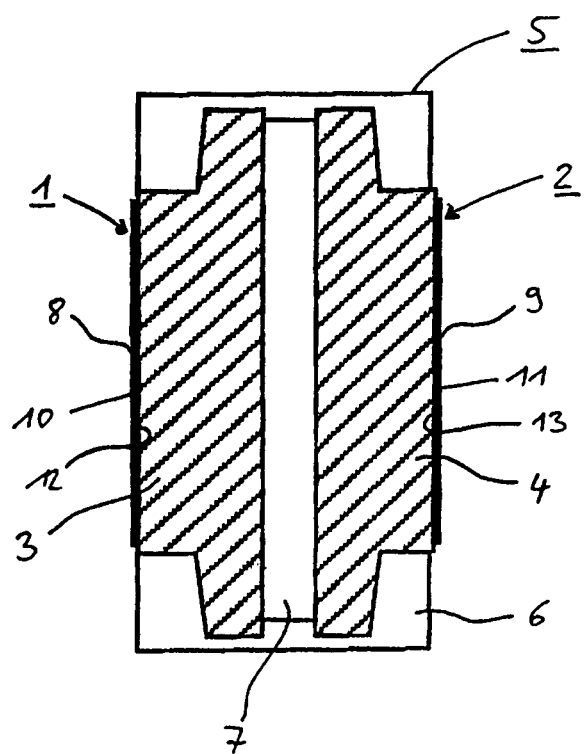
FIG. 1 is a cross-sectional view of a polymer cuvette which is equipped with electrodes produced by the method according to the invention.

FIG. 1 shows a cross-section of two formed bodies 1, 2 according to the invention, which, in this embodiment, act as electrodes 3, 4 of a cuvette 5. The cuvette 5 comprises a frame 6 which is made of a mouldable polymer and which comprises two oppositely arranged electrodes 3, 4 at the bottom. The electrodes 3, 4 are also made of a mouldable polymer which is doped with conductive substances, for example carbon fibers and/or graphite. The parallel and oppositely arranged electrodes 3, 4 include a gap-like inner chamber 7 which serves for receiving a fluid, for example an electrolyte solution. An electric current flows through the fluid and the electrolyte solution, respectively, in the inner chamber 7 when an electric voltage is applied to the electrodes 3, 4. Living cells may be suspended in the electrolyte solution and biologically active molecules, e.g. nucleic acids or proteins, which are solved in the electrolyte solution, can be introduced into the cells by means of the electric current flowing through the inner chamber 7. In order to apply a voltage the electrodes 3, 4 have to be contacted on their outer sides 8, 9 by suitable contact elements, for example a spring contact. A contact material 10, 11 having a high conductivity is tightly applied to both outer sides 8, 9 of the electrodes 3, 4 in order to avoid a burn-in of the contact elements, in particular if very high voltages are applied. In this embodiment, the contact material 10, 11 respectively covers the entire respectively available contact area 12, 13 of the electrodes 3, 4. The contact material 10, 11 can be, for example, a copper foil or a foil made of an intrinsically conductive synthetic material. The contact material 10, 11 should have a specific resistance at 23° C. below 1×10$^{-5}$ ohm×cm. Furthermore, the contact material 10, 11 must be always tightly applied to the contact areas 12, 13 in order to effectively reduce the high input resistance of the electrodes 3, 4. For this purpose, the contact material 10, 11 may be pressed, for example under pressure, onto the contact areas 12, 13, preferably under heat, wherein the temperature should be higher than the softening temperature of the polymer. Alternatively, the contact material 10, 11 may be embossed onto the contact areas 12, 13 by hot-embossing. In an alternative embodiment, the contact material 10, 11 may also be applied to the contact areas 12, 13 by means of an adhesion-mediating layer, e.g. by gluing. Due to the very tight application of the contact material 10, 11 to the contact areas 12, 13 of the electrodes 3, 4 a close, i.e. very intensive, contact between the contact material 10, 11 and the dope of the electrodes 3, 4, i.e. the conductive material within the polymer, is achieved so that the contact material 10, 11 actually provides a contact between the contact element (not shown), for example a spring contact, and the conductive material within the electrodes 3, 4. In this manner, the input resistance of the electrodes 3, 4 is significantly reduced so that less heat energy is emitted at the contact areas 12, 13, i.e. at the contactable area. Due to this measure the temperature at the contact areas 12, 13 is kept below the melting or softening point of the polymer forming the electrodes 3, 4 so that a burn-in of the contact element and the contact material is avoided. The formed bodies 1, 2 according to the invention, which are produced by the method according to the invention, can thus also advantageously used in applications wherein high voltages are used and a dot-like contacting shall, or must, be used.

Figure 2:
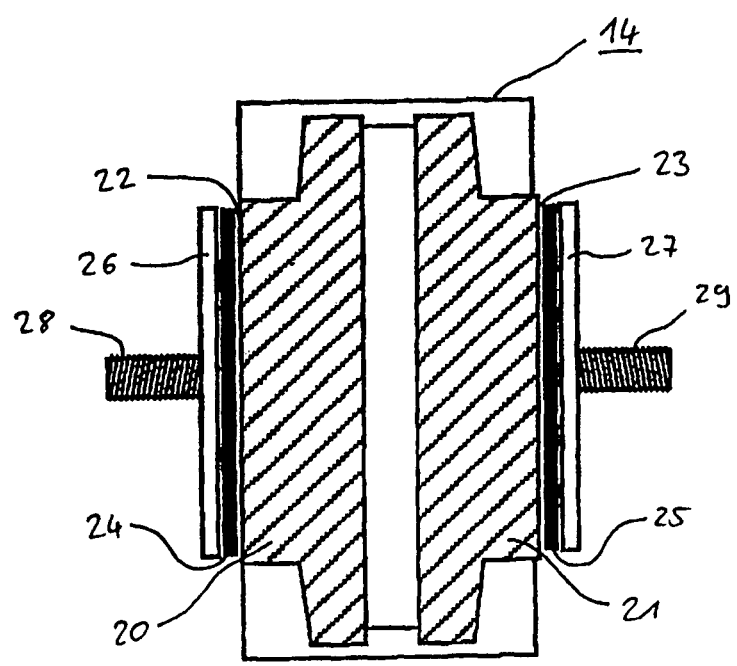
FIG. 2 shows a further embodiment of a polymer cuvette having electrodes which are produced according to the invention.

FIG. 2 shows a cross-sectional representation of a cuvette 14 which substantially corresponds to the cuvette 5 according to FIG. 1. The electrodes 20, 21 of the cuvette 14 are doped with a conductive substance as well, but comprise no foil-like contact material at their contact areas 22, 23. In this embodiment, metal plates 24, 25 are applied to the contact areas 22, 23. The metal plates 24, 25 may consist, for example, of copper. Furthermore, the metal plates 24, 25 may be heated to a temperature which is higher than the softening temperature of the polymer so that they can impress or incise into the surface of the polymer. The metal plates 24, 25 are pressed with high pressure onto the contact areas 22, 23 and vice-like loaded with a defined pressure by means of pressure plates 26, 27 which respectively comprise thread regions 28, 29. In this manner, the metal plates 24, 25 are pressed very tightly onto the contact areas 22, 23. The input resistance of the electrodes 20, 21 is hereby significantly reduced so that the metal plates 24, 25 can be contacted by means of dot-like contact elements, e.g. spring elements, without burn-in of the contact elements to the contact areas 22, 23 of the electrodes 20, 21.

Figure 3:
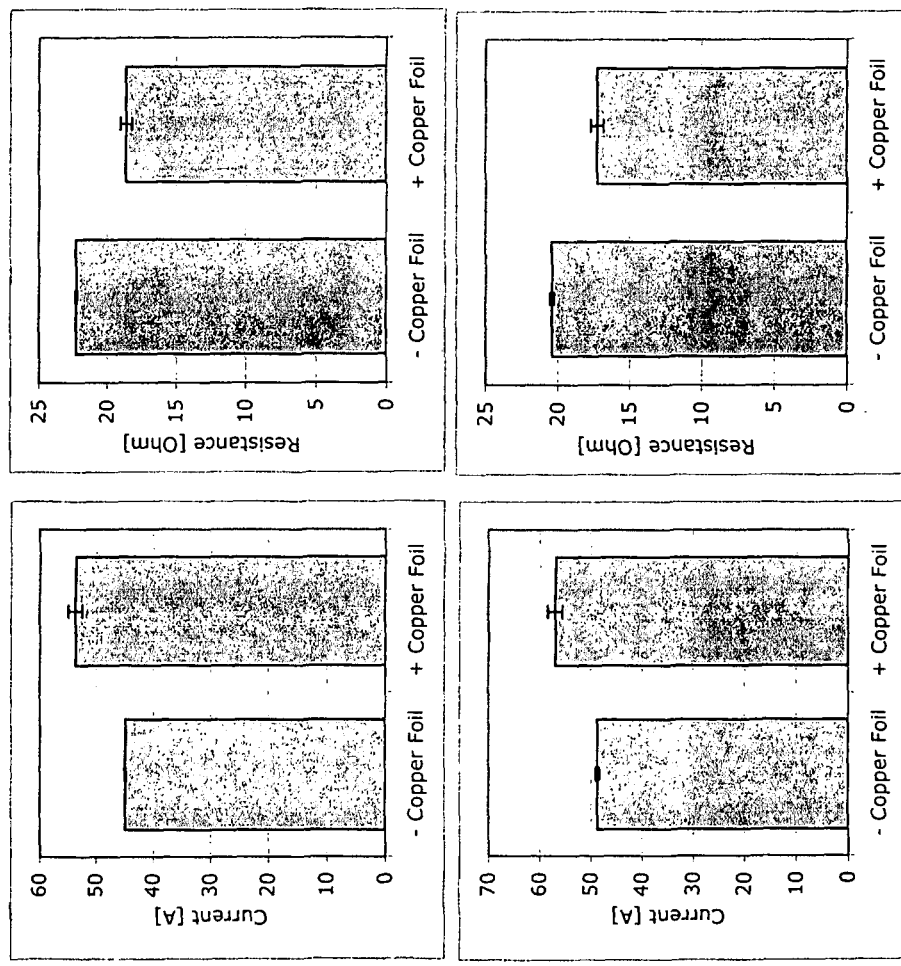
FIG. 3 shows bar diagrams of current strength and resistance, showing a comparison of the conductivity of electrodes provided with contact material and electrodes without contact material, wherein the polymer cuvettes used are equipped with electrodes made of a doped polymer (polyamide 6 with carbon fibers and graphite), and wherein the contact material is a copper foil which is applied by hot-embossing; thickness of the copper foil: 55 μm, gap length of the cuvettes: 1.5 mm, volume of the electrolyte solution within the cuvette: 100 μl, applied voltage: 1000 V Direct Voltage, A: electrolyte solution having a specific conductivity of 17.02 mS/cm, n=6

FIG. 3 shows conductivities of polymer cuvettes according to FIG. 1, which are equipped with electrodes which comprise copper foils applied by hot-embossing, compared to respective cuvettes having electrodes made of doped polymer without contact material or embossed copper foil. In the bar charts shown, it appears from the entire current flow and the measured total resistance that due to the contact material applied to the electrodes the conductivity of the electrodes is enhanced. In all experiments an enhanced current flow and a reduced total resistance could be measured when using contact material (copper foil). Since the only difference between the compared cuvettes is the contact material applied onto the contact areas of the electrodes these experiments indicate that due to the use of contact material the input resistance of the electrodes could be reduced.

FIG. 4 shows a comparison of cuvettes made of polymer according to FIG. 1. The contact material, in this embodiment a copper foil, is tightly applied to contact areas of the polymer, which have different dimensions. The comparison was conducted with different voltages. Surprisingly, in this approach it appears that a reduction of the dimension of the contact area is associated with a significant reduction of the resistance. A possible explanation of this phenomenon may be the assumption that, when narrow copper foils are used, the embossing pressure is distributed over a smaller surface area and hence a better contact with the contact material is established. This effect possibly prevails the assumed negative effect of a smaller area.

FIG. 5 shows a comparison of cuvettes according to FIG. 2 and cuvettes without integrally pressed copper plates, and cuvettes comprising a graphite layer which was inserted between the copper plates and the polymer electrodes. On the one hand, it is herewith demonstrated that by pressing of copper plates onto the electrodes made of doped polymer the resistance of the electrodes can be significantly reduced. This fact is depicted in the bar chart as enhanced current flow and reduced resistance. On the other hand, the resistance can be further reduced by insertion of a graphite layer between copper plate and polymer electrode. It can be concluded herefrom that a closer contact with the conductive material within the polymer can be established by use of the flexible graphite layer.

FIG. 6 shows a perspective view of a cuvette 30 which comprises a basic body 31 and two formed bodies 32, 33 according to the invention. The formed bodies 32, 33 are located in the narrowed regions at the bottom. The parallel arranged formed bodies 32, 33 include a gap 34 which serves for receiving, for example, a cell suspension. As can be seen with the formed body 33 a strip- or band-like contact material 35 is applied onto the formed bodies 32, 33 according to the invention. Here, the contact material 35 may be, for example, an embossed copper foil or the like. The formed bodies 32, 33 may be made of, for instance, a polymer such as polyamide 6 or polyamide 66, which is doped with carbon fibers and graphite. The formed bodies 32, 33 act as electrodes when an electric voltage is applied to the contact material 35 so that an electric field is generated within the gap 34. By means of this electric field biologically active molecules may be transferred into cells by electroporation or cells may be fused by electrofusion.

FIG. 7 shows a perspective representation of a cuvette 30 according to FIG. 6, which comprises two electrodes 36, 37 at the bottom as well. Contrary to the formed body 32, 33 according to FIG. 6, with the electrodes 36, 37 a contact material 38 completely covers the doped polymer. It is an advantage of this embodiment that a larger area is provided for contacting. The contact material 38 may be, for example, an intrinsically conductive plastic material.

LIST OF REFERENCES

1 Formed body
2 Formed body
3 Electrode
4 Electrode
5 Cuvette
6 Frame
7 Inner chamber
8 Outer sides
9 Outer sides
10 Contact material
11 Contact material
12 Contact area
13 Contact area
14 Cuvette
20 Electrode
21 Electrode
22 Contact area
23 Contact area
24 Metal plate
25 Metal plate
26 Pressure plate
27 Pressure plate
28 Thread region
29 Thread region
30 Cuvette
31 Basic body
32 Formed body
33 Formed body
34 Gap
35 Contact material
36 Electrode
37 Electrode
38 Contact material

What is claimed is:

1. Formed body made of a polymer which is doped with a conductive substance, comprising:
   at least one contactable area, within which area a contact material is applied onto said polymer, wherein said contact material
   has a lower specific resistance at 23° C. than said polymer,
   is a hot-embossed foil, and
   is applied onto said polymer so tightly that it is in close contact with said conductive substance, wherein said formed body is
   an electrode and wherein said formed body:
      is part of (a) a cuvette having a reaction chamber or (b) at least one reaction chamber of a multiwell plate,
      comprises an inner side facing said reaction chamber of (a) or (b), and
      comprises an outer side to which said contact material is applied, wherein the outer side is at an exterior surface of (a) or (b) facing away from the reaction chamber of (a) or (b).

2. The formed body according to claim 1, wherein said contact material has a specific resistance at 23° C. below $1 \times 10^{-5}$ Ohm·cm.

3. The formed body according to claim 2, wherein said contact material has a specific resistance between $1 \times 10^{-6}$ and $2 \times 10^{-6}$ Ohm·cm.

4. The formed body according to claim 1, wherein said contact material is a metal or an intrinsically conductive plastic material.

5. The formed body according to claim 1, wherein a carbon-based material or an adhesion-mediating layer having a low specific resistance is disposed between said polymer and said contact material.

6. The formed body according to claim 5, wherein said carbon-based material is at least one graphite sheet.

7. The formed body according to claim 1, wherein said polymer is doped with carbon fibers, graphite, carbon black and/or carbon nanotubes, and wherein the overall concentration of said dope in said polymer is between 50 and 80% w/w.

8. The formed body according to claim 1, wherein said polymer is polycarbonate, polyetheretherketone, polypropylene, polyamide or a mixture of these polymers.

9. The formed body according to claim 4, wherein said intrinsically conductive plastic material is polyaniline, polyacetylene, poly-para-phenylene, poly-para-phenylensulfide, polypyrroles, poly-thiophene or polypropylene.

10. The formed body according to claim 1, wherein as a result of said close contact, a temperature at the contact area between the polymer and the contact material is, when electric current flows, below a softening point of the polymer doped with the conductive substance.

11. The formed body according to claim 1, wherein the formed body has an inner side and wherein said contact material is at said outer side, but not at said inner side.

12. The formed body according to claim 1, wherein the close contact of the contact material to the polymer is configured to avoid a burn-in of a contact material even when a voltage as high as 1000 V is applied.

* * * * *